United States Patent [19]

Wrighton

[11] Patent Number: 4,929,313
[45] Date of Patent: May 29, 1990

[54] AMPEROMETRIC ELECTROCHEMICAL ION SENSORS AND METHOD FOR DETERMINING ION CONCENTRATION

[75] Inventor: Mark S. Wrighton, Winchester, Mass.

[73] Assignee: Massachusetts Institute of Technology, Cambridge, Mass.

[21] Appl. No.: 140,621

[22] Filed: Jan. 4, 1988

Related U.S. Application Data

[63] Continuation-in-part of Ser. No. 674,410, Nov. 23, 1984, Pat. No. 4,721,601, and a continuation-in-part of Ser. No. 114,566, Oct. 29, 1987.

[51] Int. Cl.⁵ .......................................... G01N 27/30
[52] U.S. Cl. .................................. 204/153.1; 204/412; 204/415; 204/418; 204/433; 204/153.13; 204/153.15; 204/153.2
[58] Field of Search ................ 204/403, 412, 415, 416, 204/418, 433, 1 T

[56] References Cited

U.S. PATENT DOCUMENTS

| | | | |
|---|---|---|---|
| 4,053,381 | 10/1977 | Hamblen et al. | 204/418 X |
| 4,214,968 | 7/1980 | Battaglia et al. | 204/418 |
| 4,263,115 | 4/1981 | Kessler et al. | 204/415 X |
| 4,272,328 | 6/1981 | Kim et al. | 204/418 X |
| 4,302,313 | 11/1981 | Columbus | 204/418 X |
| 4,303,408 | 12/1981 | Kim et al. | 204/418 X |
| 4,454,007 | 6/1984 | Pace | 204/418 X |
| 4,504,368 | 3/1985 | Delton et al. | 204/418 X |
| 4,536,274 | 8/1985 | Papadakis et al. | 204/415 X |
| 4,711,245 | 12/1987 | Higgins et al. | 204/415 X |
| 4,721,601 | 1/1988 | Wrighton et al. | 422/68 |

FOREIGN PATENT DOCUMENTS

86402169.6 4/1987 European Pat. Off. .

OTHER PUBLICATIONS

Jones et al., *J. Amer. Chem. Soc.*, (1987).

Primary Examiner—Nam X. Nguyen
Attorney, Agent, or Firm—Kilpatrick & Cody

[57] ABSTRACT

Electrochemical devices constructed according to the present invention can be used to convert an ion flux into an electric current for determination of ion concentration. The devices are operated without the need for a reference electrode and are specific based on known ion transfer agents. Operation of the devices involves the use of pairs of electrodes modified with electroactive redox materials overlaid with ion selective coatings. An applied potential between a pair of appropriately modified electrodes results in the flow of an electric current between the electrodes which is dependent on the concentration of the ion to be sensed.

Devices constructed by combining electrodes overlaid with electroactive polymers and different ion selective films allow simultaneous determination of diverse ions. For example, these devices are useful for measuring the concentration of total cations, total anions, $H^+$, $Li^+$, $K^+$, $Ca^{2+}$, $Na^+$, $HCO_3^-$, $Cl^-$, other cations and anions, and combinations thereof. The devices are small and stable enough to be used in vivo, for example, as blood monitoring means, or in large scale water quality monitoring or purification/separations techniques.

23 Claims, 1 Drawing Sheet

AMPEROMETRIC ELECTROCHEMICAL ION SENSORS AND METHOD FOR DETERMINING ION CONCENTRATION

BACKGROUND OF THE INVENTION

The present invention is an electrochemical amperometric ion sensor.

The United States Government has certain rights in this invention by virtue of Defense Advanced Research Project Agency grant No. N00014-84-K-0291 and Office of Naval Research grant No. N00014-84-K-0553.

This application is a continuation-in-part of U.S. Ser. No. 674,410 filed Nov. 23, 1984 by Mark S. Wrighton, Henry S. White and Gregg P. Kittlesen entitled "Molecule-Based Microelectronic Devices" issued Jan. 26, 1988 as U.S. Pat. No. 4,721,601 and U.S. Ser. No. 114,566 filed Oct. 29, 1987 entitled "Microelectrochemical Devices Based on Inorganic Redox Active Material" by Mark S. Wrighton.

U.S. Ser. No. 674,410 discloses several types of novel microelectrochemical devices analogous to diodes, transistors, sensors, surface energy storage elements and light emitting devices which are formed from microelectrodes overlaid with electrochemically polymerizable redox materials. The physical properties of these materials change in response to a chemical or electrical signal altering the concentration of ionic species in the polymer. Examples of the redox polymers include polypyrrole, polyaniline, polythiophene, and other materials that are conducting when oxidized and insulating when reduced.

The devices described in U.S. Pat. No. 4,721,601 are exemplified by a microelectrochemical transistor where the redox active material is an organic polymer, poly(3-methylthiophene), which connects two microelectrodes analogous to the source and drain of a conventional transistor. The essential property of the redox material is that its "conductivity" is a function of its state of charge, which can be controlled through the gate potential, $V_G$. Upon variation in $V_G$, there is a change in the drain current, $I_D$, for a fixed potential between source and drain, $V_D$, as in a solid state transistor.

Any redox material can be used to make a microelectrochemical transistor. Further, many redox materials can be expected to have a chemically sensitive "conductivity" and a chemically sensitive potential for maximum conductivity. Redox reagents are known that respond to gases ($O_2$, $H_2$, CO, etc.) and ions ($H^+$, $Li^+$, $Na^+$, etc.). However, many redox materials have such poor conductivity at any $V_G$ that measurable values of $I_D$ require spacings as small as possible between the source and drain. Additionally, since the spacing between source and drain also defines the switching speed, or response time, of the device, smaller spacings yield faster switching.

The technology for constructing microelectrochemical devices is available. The fabrication of a microelectrode array consisting of individually addressable gold or platinum microelectrodes each $\approx 2.5$ μm wide $\times \approx 50$ μm long $\times \approx 0.1$ μm high, separated from each other by $\approx 1.5$ μm, is described in U.S. Pat. No. 4,721,601. Generally, a device is constructed by providing a silicon wafer overlaid with a $SiO_2$ layer produced by thermal oxidation, overlaid with $Si_3N_4$ by low pressure chemical vapor deposition, patterning and depositing the microelectrodes using photolithography and metallization techniques known to those skilled in the art and cleaning (for example, by organic solution, MRC sputtering, and dry etching).

An alternative method, "shadow deposition", is described in an article by E. T. Jones, O. M. Chyan, and M. S. Wrighton entitled "Preparation and Characterization of Molecule-Based Transistors with a 50 Nanometer Source-Drain Separation Using Shadow Deposition Techniques: Towards Faster, More Sensitive Molecule-Based Devices" in J.Amer.Chem.Soc. (1987) and in U.S. Ser. No. 114,566 filed Oct. 29, 1987 entitled "Microelectrochemical Devices Based on Inorganic Redox Active Material" by Mark S. Wrighton. Using this method, a device with a significantly smaller spacing between microelectrodes, on the order of 50 nm, can be produced. As described, the procedure begins with a $Si_3N_4$-coated Si wafer of microelectrode arrays of eight, individually addressable gold microelectrodes each 50 microns long $\times$ 2.5 microns wide $\times$ 0.1 microns thick with spacings between microelectrodes of 1.5 microns. The first step involves a line of sight $e^-$ beam deposition of 50 nm of gold onto the wafer at an angle, closing the spacing to 50 to 100 nm. A second shadow deposition process, line of sight $e^-$ beam deposition of 100 nm of $SiO_2$ at an angle smaller than for the gold deposition step, covers the majority of the exposed gold with an insulator. The result is a set of closely-spaced (50–100 nm) microelectrodes with ultrasmall electrode areas. The total microelectrode area is estimated to be below $10^{-7}$ cm$^2$ per microelectrode.

Many redox active polymers can undergo dramatic changes, up to greater than eight orders of magnitude, in conductivity depending on their state of charge. Such materials, including polypyrrole, poly(N-methylpyrrole), poly(3-methylthiophene) and polyaniline, have been used in the construction of the first microelectrochemical devices, described in U.S. Ser. No. 674,410. The high absolute conductivity of conducting redox polymers, their good reversibility in terms of switching between their insulating and conducting states, and the ability to selectively deposit them by electrochemical methods make conducting polymers good candidates for the active material in microelectrochemical transistors. Generally, any reversible redox active molecule can be incorporated into a polymer of some sort, allowing preparation of a microelectrochemical transistor that shows a peak in $I_D$ at $V_G = E^{\circ\prime}$. For $V_G > 100$ mV away from $E^{\circ\prime}$, $I_D$ approaches zero because the self-exchange mechanism for charge transport requires a significant concentration of reduced and oxidized centers. Since $I_{D(max)}$ occurs at $E^{\circ\prime}$, the value of $I_D$ at fixed $V_G$ and $V_D$ depends on the chemical environment whenever the redox material has a chemically dependent $E^{\circ\prime}$.

Despite the tremendous potential and variety of applications made possible by the devices disclosed in U.S. Pat. No. 4,721,601, there remains a need for ion selective sensors which can operate under a variety of environmental conditions and which can be made sufficiently small, with rapid response times, to be used in vivo.

European patent application 86402169.6 by Terumo Corporation discloses an ion selective sensor formed by depositing a layer of a redox active material on an electrically conductive substrate and overlaying the redox layer with an ion selective layer. The sensor and a reference electrode are then immersed in an electrolyte solution in an electrochemical cell, the sensor is held at a constant potential with respect to the reference electrode, and the ion concentration determined by measuring the current flowing through the electrochemical cell.

The disadvantage of this system is the complexity required for it to function. A reference electrode is essential as is a means for measuring the change in current through the electrolyte. The sensor cannot be practically used in vivo or in on-line processing.

It is therefore an object of the present invention to provide novel ectrochemical devices formed with redox materials for use as ion selective sensors.

It is a further object of the present invention to provide such electrochemical devices exhibiting a reproducible proportional change in current as a function of the concentration of a particular ion such as $H^+$, $Li^+$, $Na^+$, $K^+$, $Ca^{2+}$, etc. in an analyte under a variety of conditions, including in vivo conditions.

It is still another object of the present invention to provide electrochemical devices which operate in the absence of an external reference electrode.

SUMMARY OF THE INVENTION

Amperometric electrochemical devices constructed according to the present invention can be used to convert an ion flux into an electric current for determination of ion concentration. The devices are operated. Without the need for a reference electrode and are specific based on known ion transfer agents. Operation of the devices involves the use of pairs of electrodes modified with electroactive polymers overlaid with ion selective coatings. An applied potential between a pair of appropriately modified electrodes results in the flow of an electric current in proportion to the concentration of the ion to be sensed with the device.

These devices are useful for measuring the concentration of total cations, total anions, $H^+$, $Li^+$, $K^+$, $Ca^{2+}$, $Na^+$, $HCO_3^-$, $Cl^-$, other specific cations and anions, and combinations thereof. Devices constructed by combining electrodes overlaid with electroactive polymers and different ion selective films allow simultaneous determination of different ions. The devices can be made small and stable enough to be used in vivo, for example, as blood monitoring means, or in water quality monitoring or purification/separations techniques.

BRIEF DESCRIPTION OF THE DRAWINGS

FIG. 2b is a graph of $I_D$ versus $V_D$ at pH 4 and 8 for the amperometric ion sensor of FIG. 2a.

DETAILED DESCRIPTION OF THE INVENTION

Figure 1:
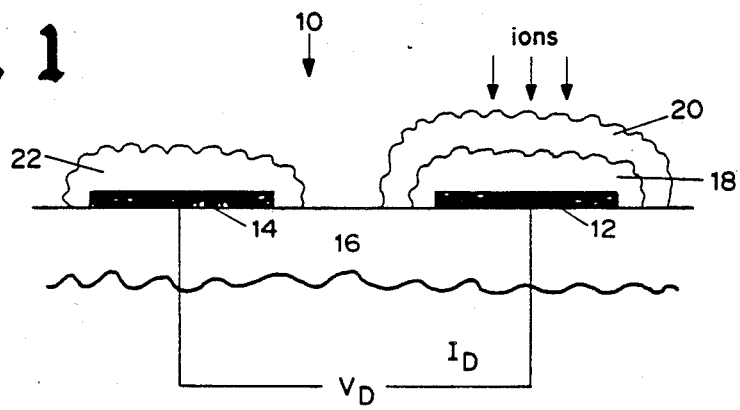
FIG. 1 is a cross-sectional schematic of an ion selective electrochemical sensor according to the present invention.

A cross sectional view of a typical electrochemical device for the determination of ion concentration in electrolyte solutions according to the present invention is illustrated in FIG. 1. The device 10 consists of a pair of electrodes 12 each of which is appropriately surface-modified with a redox polymer 14, 16 to be able to convert an ion flux through an overcoating 18 on one electrode 12a into an electric current, $I_D$, that is measurable in the external circuit 20 when a potential, $V_D$, is applied between the two electrodes 12a, 12b. Typically, the applied potential is varied linearly in time from zero as in linear sweep voltammetry.

The value of $I_D$ depends on the ion flux through the overcoat of the ion-transmitting polymer coating one of the redox polymers on one of the electrodes since ion transport into or out of the redox active material must accompany oxidation and reduction. The ion flux through the ion-transmitting layer will depend on the bulk ion concentration. Thus, whenever $I_D$ is ion fluxlimited, $I_D$ can be used to assess the concentration of the ion in solution.

A variety of redox active materials such as those described in U.S. Pat. No. 4,721,601 filed Nov. 23, 1984 or U.S. Ser. No. 114,566 filed Oct. 29, 1987 could be applied to electrodes for use in the devices of the present invention. Microelectrode, arrays are constructed as described in U.S. Pat. No. 4,721,601 or U.S. Ser. No. 114,566. The preferred redox active materials are reversible redox active polymers such as polypyrrole, poly-N-methylpyrrole, polythiophene, polyvinylferrocene, and viologens. Generally, different redox materials are used on the two electrodes, one of which is overlaid with the ion-selective coating. In the process of determining ion concentrations one redox polymer is oxidized and one is reduced. The potential at which current flows depends on the formal potentials of the two polymers. The magnitude of the current depends on the ion concentration in the bulk.

The specificity of the devices depends on using an ion-transmitting overcoat on one of the electrodes that selectively transmits the ion to be measured to the underlying redox polymer. Ion selective coatings are known to those skilled in the art. For example, a valinomycin-based coating for sensing $K^+$ can be used to produce an ion-selective electrode. Another example of a useful material is Nafion ™, E.I. DuPont de Nemours & Co., Wilmington, Del., a solid, superacidic, perfluorinated resin-sulfonic acid selective cation transmitter which is available in various configurations. A useful combination is an ionophore in polyvinylchloride. Numerous other ion-transmitting materials known to those skilled in the art can be used based on known molecules that can be derivatized to make polymer monomers. The overcoat must be free of pinholes and of uniform thickness such that a measurable $I_D$ is produced as a function of the passage of ions through the overcoating.

In its simplest form, the device of the present invention consists of two electrodes overlaid with redox active material having an ion selective coating over one of the electrodes which are directly connected by an external electrical circuit. This device is placed in the solution containing the ions to be detected and a potential is applied. By selecting a variety of polymers and coatings and combining these on a single multiple electrode array, several ions, including specific anions and cations and total anions and cations, can be simultaneously measured using a single device.

In contrast to the prior art ion sensors, the devices represented by FIG. 1 do not require a reference electrode. This is an important advantage when the device is compared to potentiometric sensors. The lack of a need for a reference electrode stems from the basic operation of the device. The only current flow corresponds to the oxidation and reduction of the surface-bound redox polymers when the value of $V_D$ is above a certain value. The "threshold" is approximated by the difference in formal potentials of the two redox active polymers. Since the ion flux-limited value of $I_D$ is the crucial feature of the device, careful control of the value of $V_D$ is not a requirement. The value of maximum $V_D$ must be such that the value of $I_D$ becomes ion flux-limited. This is accomplished by applying a sufficiently thick overcoat of the ion-transmitting film to the redox polymer.

The devices of the present invention have a number of uses. For example, they can be placed directly into the blood stream or other body fluid including fluids extracted from the lymph system or tissues and dialysates thereof, for measurement of ion concentration. In one application, the device can be used to measure $Na^+$ and $K^+$ ion concentration in the blood. In another application, the device can be used to monitor either the blood or the dialysate during kidney dialysis.

The devices can be of any size. As a result, they are also useful in water quality monitoring and in determinations of ionic strength during chemical processes including deionization, ion-exchange chromatography, and dialysis.

An amperometric ion sensor is shown schematically in FIG. 1. The sensor 10 consists of two electrodes 12, 14 on an insulating substrate 16 overlaid with redox active polymers. Electrode 12 is overlaid with a polymer 18 such as polyvinylferrocene ($PVF_c^{+/0}$) which is coated with an iontransmitting overcoat 20. Electrode 14 is overlaid with a polymer 22 such as a viologen. A potential $V_D$ is applied between the two electrodes 12, 14. $I_D$ varies as a function of the oxidation/reduction of the polymer 18 underlying the ion-transmitting overcoat 20.

EXAMPLE 1:

Construction of a [H+]Sensor.

Figure 2A:
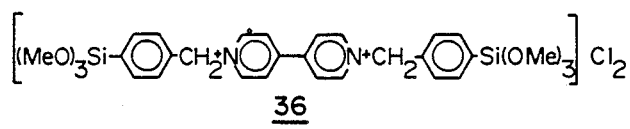
FIG. 2a is a cross-sectional schematic of an amperometric pH sensor according to the present invention consisting of an electrode, redox active viologen and ion selective polyvinylpyridine overlaying the viologen.
Figure 2A:
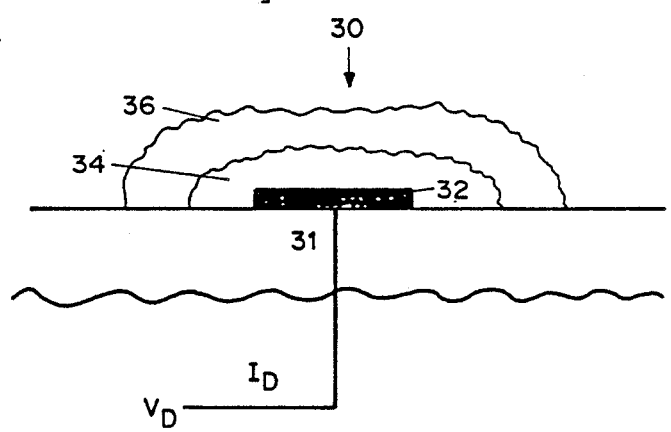

The device 30 represented in FIG. 2A was constructed by applying to one electrode 32 on an insulating substrate 31 a viologen polymer 34 overlaid with a film of polyvinylpyridine 36. The 2+ charge per monomer unit of the viologen means that two monoanionic species are bound in the polymer per monomer unit. Upon reducing the viologen polymer to the 1+state, anions must be released or cations must be taken up in order to balance charge in the viologen redox polymer.

Figure 2B:
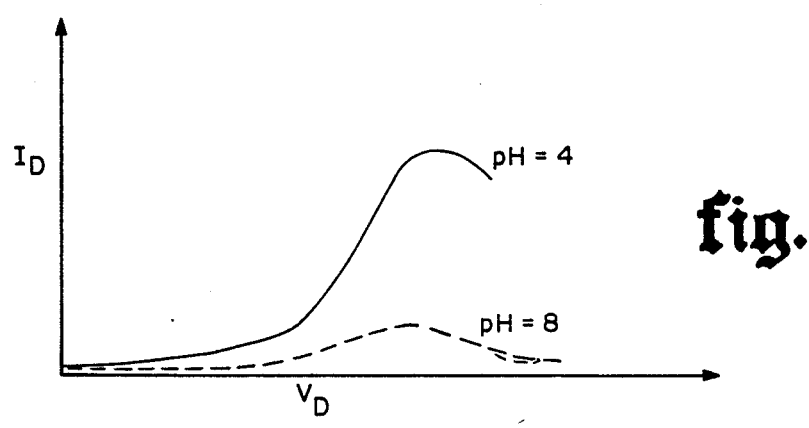

Polyvinylpyridine is "insulating" when it is not protonated. Upon protonation, the resulting polycationic material transmits ions relatively freely. FIG. 2B is a graph of representative dat for a polyvinylpyridine-coated violen redox polymer showing an increase in $I_D$ at lower pH where the polyvinylpyridine is protonated. Thus, the viologen/polyvinylpyridine bilayer represents a pH dependent device material that is specific for $H^+$.

This device, using the ion-transmitting properties of the polyvinylpyridine, demonstrates that an ion-transmitting material overcoating a redox active polymer can convert ion flux through the overcoat into a measurable electric current. Upon protonation, the polyvinylpyridine transmits the ions needed to support the reduction and oxidation of the viologen redox polymer, whereas in the non-protonated state the polyvinylpyridine allows no ion flow and hence no electric current can be detected corresponding to redox cycling of the viologen system.

Modifications and variations of the present invention, an amperometric microelectrochemical ion sensor, will be apparent to those skilled in the art from the foregoing detailed description. Such modifications and variations will be apparent to those skilled in the art.

I claim:

1. An amperometric electrochemical sensor comprising:
   a pair of electrically conductive electrodes each overlaid with electroactive polymeric material, at least one electrode having an ion-selective coating thereon, wherein said electrodes are electrically connected and said coating actively and selectively transports ions into the electroactive polymeric material effecting a change in the measured current correlated with the concentration of a substance to be measured.

2. The amperometric ion sensor of claim 1 further comprising means for applying a potential between said electrically conductive electrodes and means for measuring current between said electrodes.

3. The amperometric electrochemical ion sensor of claim 1 wherein said electroactive polymeric material is a polymer formed from electrochemically polymerizable redox active polymers.

4. The ion sensor of claim 3 wherein said polymer is selected from the group consisting of polypyrrole, poly-N-methylpyrrole, polythiophene, polyvinylferrocene, and viologens.

5. The ion sensor of claim 1 wherein said ion-selective coating is selective for cations or anions.

6. The ion sensor of claim 5 wherein the coating transmits an ion selected from the group consisting of $H^+$, $Li^+$, $K^+$, $Ca^{2+}$, $Na^+$, $HCO_3^-$ and $Cl^-$.

7. The ion sensor of claim 5 wherein the ion-selective coating is selected from the group consisting of valinomycin, Nafion ™, ionophores, and polyvinylpyridine.

8. The ion sensor of claim 1 further comprising an electrolyte.

9. The ion sensor of claim 1 further comprising additional pairs of electrodes overlaid with a different combination of electroactive polymeric materials and ion-selective coatings.

10. The sensor of claim 1 wherein the ions are the substance to be measured.

11. The sensor of claim 1 wherein the ions are indicative of the substance to be measured.

12. A method for determining ion concentration comprising providing a pair of electrically conductive electrodes each overlaid with electroactive polymeric material, at least one electrode having an ion-selective coating thereon, wherein said electrodes are electrically connected and said coating actively and selectively transports ions into the electroactive polymeric material effecting a change in the measured current correlated with the concentration of a substance to be measured.

13. The method of claim 12 further comprising providing means for applying a potential to said electrically conductive electrodes and measuring the current between said electrodes.

14. The method of claim 13 further comprising applying a potential to the electrically conductive electrodes and calculating the ion concentration from changes in current as a function of the presence of ions in the electroactive polymeric material underlying the ion-selective coating.

15. The method of claim 13 further comprising placing the electrically connected electrodes in an electrolyte and measuring pH.

16. The method of claim 13 further comprising placing the electrically conductive electrodes in a body fluid selected from the group consisting of blood, lymph, tissue extract, and dialysates thereof and measuring the change in current between said electrodes.

17. The method of claim 12 further comprising selecting the ion-selective coating to transmit cations, anions, or a specific ion.

18. The method of claim 17 wherein the coating is selected to transmit an ion selected from the group consisting of $H^+$, $Li^+$, $K^+$, $Ca^{2+}$, $Na^+$, $HCO_3^-$ and $Cl^-$.

19. The method of claim 12 further comprising providing additional pairs of electrodes overlaid with a different combination of electroactive polymeric materials and ion-selective coatings.

20. The method of claim 19 further comprising selecting the electroactive polymeric materials and ion-selective coatings to enable determination of the concentration of total cations, total anions, $H^+$, $Li^+$, $K^+$, $Ca^{2+}$, $Na^+$, $HCO_3^-$, $Cl^-$ and combinations thereof.

21. The method of claim 20 further comprising applying a potential to the electrically conductive electrodes and calculating ion concentrations from changes in current as a function of the presence of ions in the electroactive polymeric material underlying the ion-selective coatings.

22. The method of claim 12 wherein the ions are the substance to be measured.

23. The method of claim 12 wherein the ions are indicative of the substance to be measured.

* * * * *

UNITED STATES PATENT AND TRADEMARK OFFICE
CERTIFICATE OF CORRECTION

PATENT NO. : 4,929,313
DATED : May 29, 1990
INVENTOR(S) : Mark S. Wrighton It is certified that error appears in the above-identified patent and that said Letters Patent is hereby corrected as shown below:

Column 3, lines 28-29, delete the period after "operated" and replace "Without" with --without--.
Column 4, line 38, replace "Nafion TM" with --Nafion$^{TM}$--.
Column 5, line 19, replace "theY" with --they--.
Column 5, line 28, replace "(PVF$_c$+/0)" with --(PVFc$^{+/0}$)--.
Column 5, line 29, replace "iontransmitting" with --ion-transmitting--.
Column 6, Claim 7, line 36, replace "Nafion TM" with --Nafion$^{TM}$--.

Signed and Sealed this

Tenth Day of May, 1994

Attest:

BRUCE LEHMAN

*Attesting Officer*   Commissioner of Patents and Trademarks